United States Patent [19]
Makino et al.

[11] Patent Number: 6,124,351
[45] Date of Patent: Sep. 26, 2000

[54] AMINO ACID DERIVATIVES HAVING A NITRIC OXIDE SYNTHASE INHIBITING ACTION

[75] Inventors: Toshihiko Makino; Toshiaki Nagafuji, both of Shizuoka-ken, Japan

[73] Assignee: Chugai Seiyaku Kabushiki Kaisha, Tokyo, Japan

[21] Appl. No.: 08/776,928

[22] PCT Filed: Aug. 16, 1995

[86] PCT No.: PCT/JP95/01630

§ 371 Date: Feb. 11, 1997

§ 102(e) Date: Feb. 11, 1997

[87] PCT Pub. No.: WO96/06076

PCT Pub. Date: Feb. 29, 1996

[30] Foreign Application Priority Data

Aug. 18, 1994 [JP] Japan .................................. 6-228585

[51] Int. Cl.$^7$ .................................................. A61K 31/215
[52] U.S. Cl. ................................... 514/508; 558/4; 558/5
[58] Field of Search ............................ 558/5, 4; 514/508

[56] References Cited

U.S. PATENT DOCUMENTS 5,364,881  11/1994  Griffith et al. .............................. 558/5

FOREIGN PATENT DOCUMENTS 9509619  4/1995  WIPO .
9513804  5/1995  WIPO .

OTHER PUBLICATIONS

Narayanan et al., "Synthesis of L–Thiocitrulline, L–Homothiocitrulline, and S–Methyl–L–thiocitrulline: A New Class of Potent Nitric Oxide Synthase inhibitors", *J. Med. Chem.*, vol. 37, pp. 885–887, (Apr. 1994).

Feldman, Synthesis of the Putative L–Arginine Metabolite L–N–Hydroxyarginine, *Tetrahedron Letters*, vol. 32 No. 7, pp. 875–878 (Apr. 1991).

Narayanan et al., "S–Alkyl–L–thiocitrullines", *The Journal of Biological Chemistry*, vol. 270, No. 19 pp. 11103–11110, (Aug. 1995).

Nagafuji et al., "Blockade of Nitric Oxide Formation by $N^W$–Nitro–L–Arginine Mitigates Ischemic Brain Edema and Subsequent Cerebral Infarction in Rats", Neuroscience Letters, vol. 147, pp. 159–162, May 1992.

Nagafuji et al., "A Narrow Therapeutic Window of a Nitric Oxide Synthase Inhibitor Against Transient Ischemic Brain Injury", European Journal of Pharmacology, vol. 248, pp. 325–328, Jun. 1993.

Feldman, "Synthesis of the Putative L–Arginine Metabolite L–$N^G$–Hydroxyarginine", Tetrahedron Letters, vol. 32, No. 7, pp. 875–878, Apr. 1991.

Nagafuji et al., "Temporal Profiles of $Ca^{2+}$/Calmodulin–Dependent and –Independent Nitric Oxide Synthase Activity in the Rat Brain Microvessels Following Cerebral Ischemia", Acta Neuochir, vol. 60, pp. 285–288, Dec. 1994.

Narayanan et al., "Synthesis of L–Thiocitrulline, L–Homothiocitrulline, and S–Methyl–L–thiocitrulline: A New Class of Potent Nitric Oxide Synthase Inhibitors", Journal of Medicinal Chemistry, vol. 37, No. 7, pp. 885–887, Jun. 1994.

*Primary Examiner*—Samuel Barts
*Attorney, Agent, or Firm*—Browdy and Neimark

[57] ABSTRACT

Compounds represented by the general formula (I):

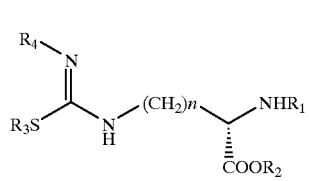

(where $R_1$ denotes a hydrogen atom, a straight-chained or branched alkoxycarbonyl group having 1–6 carbon atoms in which the alkyl portion may optionally have a substituent, or an optionally substituted straight-chained or branched acyl group having 1–9 carbon atoms;

$R_2$ denotes a hydrogen atom or an optionally substituted straight-chained or branched alkyl group having 1–6 carbon atoms;

$R_3$ denotes an optionally substituted straight-chained or branched alkyl group having 1–6 carbon atoms or an optionally substituted straight-chained or branched alkenyl group having 2–6 carbon atoms;

$R_4$ denotes a hydrogen atom;

or alternatively $R_3$ and $R_4$ may combine together to form an optionally substituted 5- to 7-membered ring; and n denotes an integer of 2–4, provided that when $R_3$ is a methyl group, n is not 3 at the same time) or pharmaceutically acceptable salts thereof.

8 Claims, No Drawings

AMINO ACID DERIVATIVES HAVING A NITRIC OXIDE SYNTHASE INHIBITING ACTION

This application is a 371 of PCT/JP95/01630 filed Aug. 16, 1995.

TECHNICAL FIELD

This invention relates to amino acid derivatives, more specifically to the compounds represented by the general formula (I) which have an inhibitory effect on nitric oxide synthase (hereunder abbreviated as NOS) to suppress the production of nitric oxide (hereunder abbreviated as NO) and thereby prove effective against the pathology in an acute phase of cerebrovascular disorders, in particular, occlusive cerebrovascular disorders in which NO or its metabolites would be involved, or pharmaceutically acceptable salts thereof. The invention also relates to preventives and therapeutics of such disorders and symptoms that comprise said compounds or pharmaceutically acceptable salts thereof as an effective ingredient.

BACKGROUND ART

In the brain region where blood flow is interrupted, cytotoxic brain edema occurs first, followed by vasogenic brain edema. Vasogenic brain edema developes several hours after the occurrence of cerebral ischemia and its progress continues for one week from the onset. Thereafter, brain edema decreases gradually and, depending on the focal range of infarction, the edema persists as an infarcted area for one to three months. Since the brain is covered with the rigid skull, cerebral edema causes an increase in the brain volume. If the cerebral edema exceeds a certain limit, there occurs an abrupt increase in the tissue pressure and the intracranical pressure, often inducing fatal hernia and eventually aggravating the encephalopathy to determine the scope of the subsequent infarcted area (Siesjö, J. Neurosurg. 77, 169–184, 1992). Thus, the treatment of cerebral edema which is critical to the patient's life and the prognosis of his disease is clinically a very important objective. The three primary methods currently used to treat cerebral edema are hyperpnea, the drainage of cerebrospinal fluid and the use of hypertonic solutions, steroids or the like; however, in almost all cases, these methods provide only temporary ameliorative effects and there is not much promise for the therapeutic efficacy to be finally achieved (Siesjö, J. Neurosurg. 77, 337–354, 1992). Therefore, it has been desirable to develop drugs that have an entirely different mechanism of action and which will prove effective in the treatment of ischemic cerebrovascular disorders.

The present inventors previously found that $N^G$-nitro-L-arginine (L-NNA), a NOS inhibitor, was capable of ameliorating cerebral edema and infarction that were developed after focal cerebral ischemia (Nagafuji et al., Neurosci. Lett., 147, 159–162, 1992), as well as the neuronal cell death that was also developed after transient global cerebral ischemia (Nagafuji et al., Eur. J. Pharmacol. Env. Tox., 248, 325–328, 1993). However, it has also been reported that relatively high doses of NOS inhibitors are not only ineffective against ischemic brain damage but also they sometimes aggravate it (Iadecola et al., J. Cereb. Blood Flow Metab., 14, 175–192, 1994).

A presently dominant theory based on genetic DNA analyses holds that NOS exists in at least three isoforms, namely, N-cNOS which is mainly present constitutively in neurons, E-cNOS which is mainly present constitutively in vascular endothelial cells, and iNOS which is induced from transcriptional level on stimulation by cytokines and/or endotoxins in macrophages and other cells. Among these three isoforms, N-cNOS and E-cNOS are calcium-dependent whereas iNOS is not calcium-dependent (Nathan et al., FASEB J., 16, 3051–3064, 1992).

A mechanism that has been proposed as being most probable for explaining disorders in the brain tissue which accompany cerebral ischemia is a pathway comprising the sequence of elevation in the extracellular glutamic acid level, hyperactivation of glutamic acid receptors on the post-synapses, elevation in the intracellular calcium level and abnormal activation of calcium-dependent enzymes (Siesjö, J. Cereb. Blood Flow Metab. 1, 155–185, 1981; Siesjö, J. Neurosurg. 60, 883–908, 1984; Choi, Trends Neurosci. 11, 465–469, 1988; Siesjo and Bengstsson, J. Cereb. Blood Flow Metab. 9, 127–140, 1989). As already mentioned, N-cNOS is calcium-dependent, so the inhibition of abnormal activation of this type of NOS isoform would contribute to the neuroprotective effects of NOS inhibitors (Dawson et al., Annals Neurol. 32, 297–311, 1992).

It is also known that NO is at least one of the essences of endothelium-derived relaxing factor (EDRF), so if E-cNOS is inhibited by a more-than-necessary degree, the cerebral vasculare will be constricted and the blood flow will decrease whereas the blood pressure will increase, thereby aggravating the dynamics of micro-circulation, possibly leading to an expansion of the ischemic lesion.

Therefore, if a therapeutic for ischemic cerebral diseases is to be developed, a NOS inhibitor is desirable that inhibits E-cNOS only weakly but which strongly inhibits N-cNOS (Nowicki et al., Eur. J. Pharmacol., 204, 339–340, 1991; Dawson et al., Proc. Natl. Acad. Sci. USA, 88, 6368–6371, 1991). No reports have yet been published showing that certain of the NOS inhibitors highly selectively for N-cNOS in comparison with the E-cNOS inhibiting action in the manner just described above.

Upon stimulation by certain kinds of cytokines and/or endotoxins, iNOS is induced in immunocytes such as macrophages and glial cells and other cells, and the resulting large amount of NO will cause a fatal drop in blood pressure. Therefore, it is speculated that an iNOS selective inhibitor may be effective against hypotension and other symptoms of sepsis (Kilbourn and Griffith, J. Natl. Cancer Inst. 84, 827–831, 1992; Cobb et al., Crit. Care Med. 21, 1261–1263, 1993; Lorente et al., Crit. Care Med. 21, 1287–1295, 1993).

Aminoguanidine (AG) is the only compound that has ever been reported to show selectivity for iNOS in comparison with the E-cNOS inhibiting action (Griffith et al., Br. J. Pharmacol. 110, 963–968, 1993); however, the inhibiting potency and selectivity for iNOS of this compound is insufficient to warrant its use as a therapeutic effective against hypotension in sepsis.

DISCLOSURE OF INVENTION

An object of the present invention is to provide compounds that are capable of selective inhibition of specified NOS isoforms to prove effective against diseases in which the involvement of excess NO or its metabolites is suggested. Stated more specifically, the invention provides the NOS inhibitors that have a weak E-cNOS inhibiting action but which strongly inhibit N-cNOS, thereby proving useful as treatment for cerebrovascular disorders. The invention also provides the NOS inhibitors that have an iNOS selective inhibiting action to thereby prove effective against hypotension in sepsis.

The present inventors conducted intensive studies with a view to attaining the stated object; as a result, we found that among the compounds represented by the general formula (I), those in which $R_3$ was halogen-atom substituted straight-chained or branched alkyl groups having 1–6 carbon atoms or salts thereof had a by far superior N-cNOS selective inhibiting action over the commonly recognized NOS inhibitors and hence, were useful as a therapeutics of cerebrovascular disorders; the present invention has been accomplished on the basis of this finding. In addition, the present inventors found that among the compounds represented by the general formula (I), the one in which $R_3$ was an allyl group or salts thereof had a by far superior iNOS selective inhibiting action over the commonly recognized NOS inhibitors and, hence, was useful for treating sepsis; the present invention has been accomplished on the basis of this finding.

Thus, the present invention provides the compounds set forth in (1)–(6) below or pharmaceutically acceptable salts thereof.

(1) A compound represented by the general formula (I):

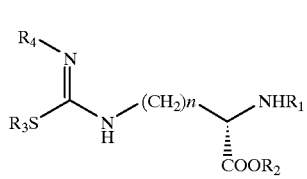

(where
$R_1$ denotes a hydrogen atom, a straight-chained or branched alkoxycarbonyl group having 1–6 carbon atoms in which the alkyl portion may optionally have a substituent, or an optionally substituted straight-chained or branched acyl group having 1–9 carbon atoms;

$R_2$ denotes a hydrogen atom or an optionally substituted straight-chained or branched alkyl group having 1–6 carbon atoms;

$R_3$ denotes an optionally substituted straight-chained or branched alkyl group having 1–6 carbon atoms or an optionally substituted straight-chained or branched alkenyl group having 2–6 carbon atoms;

$R_4$ denotes a hydrogen atom;

or alternatively $R_3$ and $R_4$ may combine together to form an optionally substituted 5- to 7-membered ring; and n denotes an integer of 2–4, provided that when $R_3$ is a methyl group, n is not 3 at the same time) or a pharmaceutically acceptable salt thereof.

(2) A compound as set forth in (1) which is represented by the general formula (I):

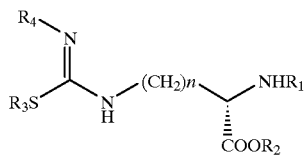

(where
$R_1$ denotes a hydrogen atom, a straight-chained or branched alkoxycarbonyl group having 1–6 carbon atoms in which the alkyl portion may optionally have a substituent, or an optionally substituted straight-chained or branched acyl group having 1–9 carbon atoms;

$R_2$ denotes a hydrogen atom or an optionally substituted straight-chained or branched alkyl group having 1–6 carbon atoms;

$R_3$ denotes a halogen-atom substituted straight-chained or branched alkyl group having 1–6 carbon atoms;

$R_4$ denotes a hydrogen atom; and n denotes an integer of 2–4) or a pharmaceutically acceptable salt thereof.

(3) A compound as set forth in (1) which is represented by the general formula (I):

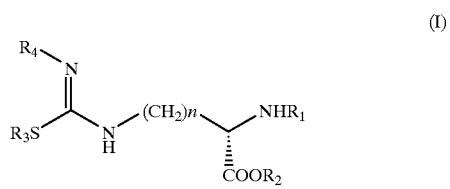

(where
$R_1$ denotes a hydrogen atom, a straight-chained or branched alkoxycarbonyl group having 1–6 carbon atoms in which the alkyl portion may optionally have a substituent, or an optionally substituted straight-chained or branched acyl group having 1–9 carbon atoms;

$R_2$ denotes a hydrogen atom or an optionally substituted straight-chained or branched alkyl group having 1–6 carbon atoms;

$R_3$ denotes a 2-fluoroethyl group;

$R_4$ denotes a hydrogen atom; and n denotes an integer of 2–4) or a pharmaceutically acceptable salt thereof.

(4) A compound as set forth in (1) which is represented by the general formula (I):

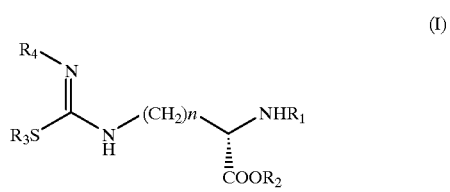

(where
$R_1$ and $R_2$ each independently denote a hydrogen atom;

$R_3$ denotes an optionally substituted straight-chained or branched alkyl group having 1–6 carbon atoms or an optionally substituted straight-chained or branched alkenyl group having 2–6 carbon atoms;

$R_4$ denotes a hydrogen atom;

or alternatively $R_3$ and $R_4$ may combine together to form an optionally substituted 5- to 7-membered ring; and n denotes an integer of 2–4, provided that when $R_3$ is a methyl group, n is not 3 at the same time) or a pharmaceutically acceptable salt thereof.

(5) A compound as set forth in (1) which is selected from the group of compounds consisting of δ-(S-(2 fluoroethyl) isothioureido)-L-norvaline, δ-(Sethylisothioureido)-L-norvaline and δ-(S-(3-chloropropyl)isothioureido)-L-norvaline, or a pharmaceutically acceptable salt thereof.

(6) A compound as set forth in (1) which is δ-(S-allylisothioureido)-L-norvaline, or a pharmaceutically acceptable salt thereof.

In particular, δ-(S-(2-fluoroethyl)isothioureido)-L-norvaline and δ-(S-ethylisothioureido)-L-norvaline have a by far superior N-cNOS selective inhibitory effect over the existing NOS inhibitors and yet they have a weak E-cNOS inhibitory effect; hence, they are useful as treatment for cerebrovascular disorders.

In addition, δ-(S-allylisothioureido)-L-norvaline has a by far superior iNOS selective inhibitory effect over the existing NOS inhibitors and hence is useful as therapy for sepsis.

BEST MODE FOR CARRYING OUT THE INVENTION

The compounds of the invention which are represented by the general formula (I) are yet to be documented novel compounds and may typically be produced as follows.

Alternatively, a compound represented by the general formula (II) (where $R_1$ denotes a straight-chained or branched alkoxycarbonyl group having 1–6 carbon atoms in which the alkyl portion may optionally have a substituent or an optionally substituted straight-chained or branched acyl group having 1–9 carbon atoms; $R_2$ denotes an optionally substituted straight-chained or branched alkyl group having 1–6 carbon atoms; and n denotes an integer of 2–4) may be reacted with a compound of the general formula (V) (where $R_5$ denotes an optionally substituted alkylene group having 2–4 carbon atoms; X denotes a halogen atom; and Y denotes a halogen atom or an alkoxycarbonyl group having 1–6 carbon atoms) in a solvent such as acetonitrile, acetone, 1,4-dioxane, methanol or ethanol at a temperature from room temperature to the boiling point of the reaction mixture. Preferably, the reaction mixture is refluxed in acetonitrile.

Then, hydrolysis or deprotection by direct treatment with a deprotecting agent is performed to yield either a compound represented by the general formula (VI) (where $R_1$, and $R_2$

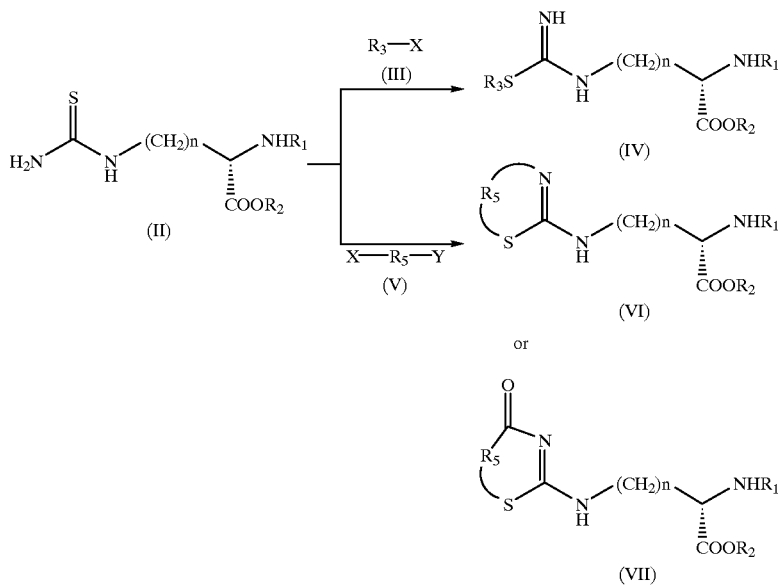

The respective reaction schemes are explained below.

A compound represented by the general formula (II) (where $R_1$ denotes a straight-chained or branched alkoxycarbonyl group having 1–6 carbon atoms in which the alkyl portion may optionally have a substituent or an optionally substituted straight-chained or branched acyl group having 1–9 carbon atoms; $R_2$ denotes an optionally substituted straight-chained or branched alkyl group having 1–6 carbon atoms; and n denotes an integer of 2–4) may be reacted with a compound of the general formula (III) (where $R_3$ denotes an optionally substituted straight-chained or branched alkyl group having 1–6 carbon atoms or an optionally substituted straight-chained or branched alkenyl group having 2–6 carbon atoms, provided that when n in the general formula (II) is 3, $R_3$ is not a methyl group; and X denotes a halogen atom) in a solvent such as acetonitrile, acetone, 1,4-dioxane, methanol or ethanol at a temperature from room temperature to the boiling point of the reaction mixture. Preferably, the reaction mixture is refluxed in acetonitrile.

Then, hydrolysis or deprotection by direct treatment with a deprotecting agent is performed to yield a compound represented by the general formula (IV) (where $R_1$ and $R_2$ denote a hydrogen atom, and n denotes an integer of 2–4) or a salt thereof.

denote a hydrogen atom; $R_5$ denotes an optionally substituted alkylene group having 2–4 carbon atoms or such an alkylene group having a terminal carbonyl group bound thereto; and n denotes an integer of 2–4) or a compound represented by the general formula (VII) (where $R_1$, $R_2$, $R_5$ and n are as defined above) or salts thereof.

The deprotecting reaction is carried out under appropriate conditions depending on the types of the protecting groups used. For example, if $R_1$ is a benzyl-oxycarbonyl group and $R_2$ is a benzyl group, a catalytic reduction may be performed at room temperature in a solvent such as ethyl acetate, methanol or ethanol in the presence of palladium-carbon. If $R_1$ is a t-butoxycarbonyl group and $R_2$ is a t-butyl group, the reaction is preferably carried out using a deprotecting agent such as trifluoroacetic acid, hydrochloric acid, sulfuric acid or methanesulfonic acid in a solvent that will cause no adverse effects on the reaction such as methylene chloride, ethyl acetate, methanol, ethanol, 1,4-dioxane or water, or without using any solvent at a temperature from 0° C. to room temperature, and the use of trifluoroacetic acid at room temperature under dry conditions is particularly preferred.

In the definitions of the general formulae (I), (II), (III), (IV), (V), (VI) and (VII), examples of the straight-chained or branched alkoxycarbonyl group having 1–6 carbon atoms in which the alkyl portion may optionally have a substituent include a benzyloxycarbonyl group, a t-butoxycarbonyl group and a 9-fluorenylmethyloxycarbonyl group; examples of the optionally substituted straight-chained or branched acyl group having 1–9 carbon atoms include an acetyl group. A particularly preferred example of $R_1$ is a t-butoxycarbonyl group. Examples of the optionally substituted straight-chained or branched alkyl group having 1–6 carbons include a methyl group, an ethyl group and a t-butyl group. Examples of the substituents on the optionally substituted straight-chained or branched alkyl group having 1–6 carbon atoms, as well as on the optionally substituted straight-chained or branched alkenyl groups having 2–6 carbon atoms include halogens, an alkyl group and an aryl group, preferably a fluorine atom, a cyclopropyl group, etc. A particularly preferred example of $R_2$ is a t-butyl group. Examples of $R_3$ include a 2-fluoroethyl group, a cyclopropylmethyl group and a phenyl group, preferably the 2-fluoroethyl group. Examples of the optionally substituted straight-chained or branched alkenyl group having 2–6 carbon atoms include a 1-propenyl group. A preferred example of X is a chlorine atom, a bromine atom or an iodine atom. A preferred example of Y is a chlorine atom, a bromine atom, an iodine atom, a methoxycarbonyl group or an ethoxycarbonyl group. Examples of the optionally substituted alkylene group having 2–4 carbon atoms include an ethylene group and a propylene group. Preferred examples of $R_5$ are an ethylene group and a propylene group.

Pharmaceutically acceptable salts of the invention compound (I) include organic acid salts such as acetates, maleates, tartrates, methanesulfonates, benzenesulfonates, formates, p-toluenesulfonates and trifluoroacetates, and inorganic acid salts such as hydrochlorides, sulfates, hydrobromides and phosphates, preferably the dihydrochlorides.

The following examples are provided for the purpose of further illustrating the production of the compounds of the invention but are not in any way to be taken as limiting.

In addition, in order to demonstrate the utility of the invention, the action of compounds of the general formula (I) in selectively inhibiting various kinds of NOS was tested and the results are shown below.

EXAMPLES

Example 1

Synthesis of α-N-t-butoxycarbonyl-δ-(S-ethylisothioureido)-L-norvaline-t-butyl ester hydroiodide A mixture of α-N-t-butoxycarbonyl-δ-thioureido-L-norvaline-t-butyl ester (0.48 g) synthesized as described by Paul L. Felderman (Tetrahedron Lett., 32, 7, 875–878, 1991), and acetonitrile (5 ml) was added ethyl iodide (0.17 ml) and the reaction mixture was refluxed for 2 h. The reaction mixture was concentrated under reduced pressure and, thereafter, the residue was purified by silica gel column chromatography (developing solution, methylene chloride:methanol=95:5) to yield 0.67 g of α-N-t-butoxycarbonyl-δ(S-ethylisothioureido)-L-norvaline-t-butyl ester hydroiodide.

$^1$H-NMR(CDCl$_3$); δ: 1.39–1.47(12H,m), 1.48(9H,s), 1.63–1.97(4H,m), 3.36–3.62(4H,m), 4.07–4.19(1H,m), 5.22–5.41(1H,m); FAB-MS(m/Z)376(M$^+$+1)

Example 2

Synthesis of δ-(S-ethylisothioureido)-L-norvaline

A mixture of α-N-t-butoxycarbonyl-δ-(S-ethylisothioureido )-L-norvaline-t-butyl ester hydroiodide (0.67 g) and trifluoroacetic acid (5 ml) was stirred at room temperature for 2 h and concentrated under reduced pressure. The residue was dissolved in ethanol and 4N solution of hydrogen chloride in 1,4-dioxane (1 ml) was added to the ethanol solution at room temperature and the reaction mixture was evaporated. The residue was purified by ion-exchange chromatography (DOWEX, 50W-X8, H+ form) to yield 0.25 g of δ-(S-ethylisothioureido)-L-norvaline.

$^1$H-NMR(D$_2$O); δ: 1.30–1.35(3H,m), 1.56–1.89(4H,m), 3.03–3.10(2H,m), 3.35–3.38(2H,m), 3.43–3.50(1H,m) FAB-MS(m/z)220(M$^+$+1)

Example 3

Synthesis of α-N-t-butoxycarbonyl-δ-(S-(2-fluoroethyl) isothioureido)-L-norvaline-t-butyl ester hydrobromide Using 2-fluoroethyl bromide as a reagent, the same reaction as Example 1 was performed to yield 0.29 g of α-N-t-butoxycarbonyl-δ-(S-(2-fluoroethyl) isothioureido)-L-norvaline-t-butyl ester hydrobromide.

$^1$H-NMR(CDCl$_3$); δ: 1.44(9H,s), 1.48(9H,s), 1.62–1.96 (4H,m), 3.38–3.61(2H,m), 3.77(2H,destorted dt, J=25.1 Hz, 4.95–5.28H), 4.03–4.19(1H,m), 4.75(2H,destorted dt, J=46.9 Hz, 4.95–5.28 Hz), 5.24–5.37(1H,m); FAB-MS(m/z)394(M$^+$+1)

Example 4

Synthesis of δ-(S-(2-fluoroethyl)-isothioureido)-L-norvaline dihydrochloride

A mixture of the compound obtained in Example 3 and trifluoroacetic acid (10 ml) was stirred at room temperature for 2 h and thereafter concentrated under reduced pressure. The residue was dissolved in ethanol (5 ml) and thereafter 4N solution of hydrogen chloride in 1,4-dioxane (0.6 ml) was added to the ethanol solution at room temperature and the reaction mixture was evaporated. The residue was dissolved in water and thereafter freeze-dried to yield 0.17 g of δ-(S-(2-fluoroethyl)isothioureido)-L-norvaline dihydrochloride.

$^1$H-NMR(D$_2$O); δ: 1.76–2.06(4H,m), 3.43–3.56(4H,m), 4.05–4.09(1H,m), 4.80(2H,destorted dt,J=46.5 Hz, 4.95–5.61 Hz); FAB-MS(m/z)238(M$^+$+1)

Example 5

Synthesis of α-N-t-butoxycarbonyl-δ-(S-(2-propenyl) isothioureido)-L-norvaline-t-butyl ester hydrobromide Using allyl bromide as a reagent, the same reaction as Example 1 was performed to yield 0.51 g of α-N-t-butoxycarbonyl-δ-(S-(2-propenyl)isothioureido )-L-norvaline-t-butyl ester hydrobromide.

$^1$H-NMR(CDCl$_3$); δ: 1.44(9H,s), 1.47(9H,s), 1.67–1.99 (4H,m), 3.32–3.63(4H,m), 3.81–3.91(1H,m), 3.99–4.18(2H, m), 5.35–5.44(1H,m); FAB-MS(m/z)388(M$^+$+1)

Example 6

Synthesis of δ-(S-(2-propenyl)isothioureido)-L-norvaline dihydrochloride

Using as a starting material the compound obtained in Example 5, a deprotection was performed as in Example 4 to yield 0.33 g of δ-(S-(2-propenyl)isothioureido)-L-norvaline dihydrochloride.

¹H-NMR(D₂O); δ: 1.72–2.09(4H,m), 3.41–3.46(2H,m), 3.78(2H,d,J=6.8 Hz), 4.07–4.12(1H,m), 5.26–5.40(2H,m), 5.85–5.99(1H,m); FAB-MS(m/z)232(M⁺+1)

Example 7

Synthesis of α-N-t-butoxycarbonyl-δ-( 2,3-dehydrothiazolin-2-yl)amino-L-norvaline-t-butyl ester hydrobromide Using 1,2-dibromoethane as a reagent, the same reaction as Example 1 was performed to yield 0.23 g of α-N-t-butoxycarbonyl-δ-(2,3-dehydrothioazolin-2-yl)amino-L-norvaline-t-butyl ester hydrobromide.

¹H-NMR(CDCl₃); δ: 1.44(9H,s), 1.47(9H,s), 1.67–1.99 (4H,m), 3.32–3.63(4H,m), 3.81–3.91(1H,m), 3.99–4.18(2H, m), 5.35–5.44(1H,m); FAB-MS(m/z)374(M⁺+1)

Example 8

Synthesis of δ-(2,3-dehydrothiazolin-2-yl)amino-L-norvaline dihydrochloride

Using as a starting material the compound obtained in Example 7, a deprotection reaction was performed as in Example 4 to yield 0.11 g of δ-(2,3-dehydrothiazolin-2-yl) amino-L-norvaline dihydrochloride.

¹H-NMR(D₂O); δ: 1.68–1.89(4H,m), 3.28–3.49(4H,m), 3.98–4.04(1H,m), 4.69–4.78(2H,m); FAB-MS(m/z)218 (M⁺+1)

Example 9

Synthesis of α-N-t-butoxycarbonyl-ε-(S-methylisothioureido )-L-norleucine-t-butyl ester hydroiodide Using α-N-t-butoxycarbonyl-ε-thioureido-L-norleucine-t-butyl ester (0.19 g) synthesized as described by K. Narayanan (J. Med. Chem., 37, 885–887, 1994) as a starting material and methyl iodide as a reagent, the same reaction as Example 1 was performed as to yield 0.29 g of α-N-t-butoxycarbonyl-ε-(S-methylisothioureido )-L-norleucine-t-butyl ester hydroiodide.

¹H-NMR(CDCl₃); δ: 1.44(9H,s), 1.47(9H,s), 1.67–1.85 (6H,m), 2.81(3H,s), 3.32–3.53(2H,m), 4.05–4.18(1H,m), 5.16–5.27(1H,m); FAB-MS(m/z)376(M⁺+1)

Example 10

Synthesis of ε-(S-methylisothioureido)-L-norleucine dihydrochloride

Using as a starting material the compound obtained in Example 9, a deprotection was performed as in Example 4 to yield 0.15 g of ε-(S-methylisothioureido)-L-norleucine dihydrochloride.

¹H-NMR(D₂O); δ: 1.42–1.64(2H,m), 1.68–1.81(2H,m), 1.90–2.10(2H,m), 2.60(3H,s), 3.38–3.43(2H,m), 4.09(1H,t, J=6.3 Hz); FAB-MS(m/z)220(M⁺+1)

Example 11

Synthesis of α-N-t-butoxycarbonyl-δ-( S-(n-propyl) isothioureido)-L-norvaline-t-butyl ester hydroiodide Using n-propyl iodide as a reagent, the same reaction as Example 1 was performed to yield 0.75 g of α-N-t-butoxycarbonyl-δ-(S-(n-propyl)isothioureido)-L-norvaline-t-butyl ester hydroiodide.

¹H-NMR(CDCl₃); δ: 1.09(3H,t,J=7.3 Hz), 1.44(9H,s), 1.48(9H,s), 1.77–1.92(6H,m), 3.33–3.38(2H,m), 3.39–3.72 (2H,m), 4.05–4.17(1H,m), 5.20–5.52(1H,m);

Example 12

Synthesis of δ-(S-(n-propyl)isothioureido)-L-norvaline

Using as a starting material the compound obtained in Example 11, the same procedure as Example 2 yielded 0.31 g of δ-(S-(n-propyl)isothioureido)-L-norvaline.

¹H-NMR(DMSO-d₆); δ: 0.95(3H,t,J=7.3 Hz), 1.54–1.67 (6H,m), 1.92–2.02(2H,m), 3.13–3.30(2H,m), 4.17–4.27(1H, m); FAB-MS(m/z)234(M⁺+1)

Example 13

Synthesis of α-N-t-butoxycarbonyl-δ-(4H-5,6-dihydro-1,3-thiazin-2-yl) amino-L-norvaline-t-butyl ester hydrobromide Using 1,3-dibromopropane as a reagent, the same reaction as Example 1 was performed to yield 0.19 g of α-N-t-butoxycarbonyl-δ-(4H-5,6-dihydro-1,3-thiazin-2-yl)amino-L-norvaline-t-butyl ester hydrobromide.

¹H-NMR(CDCl₃); δ: 1.44(9H,s), 1.46(9H,s), 1.55–1.91 (4H,m), 2.06–2.18(2H,m), 2.96–3.00(2H,m), 3.29(2H,t,J= 5.6 Hz), 4.11–4.23(1H,m), 5.39–5.48(1H,m); FAB-MS(m/z)388(M⁺+1)

Example 14

Synthesis of δ-(4H-5,6-dihydro-1,3-thiazin-2-yl) amino-L-norvaline

Using as a starting material the compound obtained in Example 13, the same procedure as Example 2 yielded 0.13 g of δ-(4H-5,6-dihydro-1,3-thiazin-2-yl)amino-L-norvaline.

¹H-NMR(D₂O); δ: 1.69–1.81(6H,m), 2.20–2.28(2H,m), 3.17–3.30(2H,m), 3.55–3.73(3H,m), FAB-MS(m/z)232 (M⁺+1)

Example 15

Synthesis of α-N-t-butoxycarbonyl-δ-(2,3-dehydro-4-oxothiazolin-2-yl)amino-L-norvaline-t-butyl ester Using methyl bromoacetate as a reagent, the same reaction as Example 1 was performed to yield 0.28 g of α-N-t-butoxycarbonyl-δ-(2,3-dehydro-4-oxothiaozolin-2-yl)amino-L-norvaline-t-butyl ester.

¹H-NMR(CDCl₃); δ: 1.44(9H,s), 1.46(9H,s), 1.61–1.78 (4H,m), 3.35–3.40(2H,m), 3.86(2H,s), 4.11–4.26(1H,m); FAB-MS(m/z)388(M⁺+1)

Example 16

Synthesis of δ-(2,3-dehydro-4-oxothiazolin-2-yl) amino-L-norvaline

Using as a starting material the compound obtained in Example 15, the same procedure as Example 2 yielded 0.12 g of δ-(2,3-dehydro-4-oxothiazolin-2-yl)amino-L-norvaline.

¹H-NMR(D₂O); δ: 1.74–1.93(4H,m), 3.42–3.57(2H,m), 3.72–3.76(1H,m), 4.06(2H,s); FAB-MS(m/z)232(M⁺+1)

Example 17

Synthesis of α-N-t-butoxycarbonyl-δ-(S-(cyclopropylmethyl) isothioureido)-L-norvaline-t-butyl ester hydrobromide Using cyclopropylmethyl bromide as a reagent, the same reaction was as Example 1 performed to yield 0.54 g of α-N-t-butoxycarbonyl-δ-(S-(cyclopropylmethyl) isothioureido)-L-norvaline-t-butyl ester hydrobromide.

$^1$H-NMR(CDCl$_3$); δ: 0.38–0.49(2H,m), 0.63–0.75(2H,m), 1.00–1.18(1H,m), 1.48(9H,s), 1.76(9H,s), 1.62–1.96 (4H,m), 3.34(2H,d,J=7.6 Hz), 3.36–3.53(2H,m), 4.07–4.21 (1H,m), 5.20–5.33(1H,m); FAB-MS(m/z)402(M$^+$+1)

Example 18

Synthesis of δ-(S-(cyclopropylmethyl) isothioureido)-L-norvaline dihydrochloride Using as a starting material the compound obtained in Example 17, a deprotection was performed as in Example 4 to yield 0.36 g of δ-(S-(cyclopropylmethyl)isothioureido)-L-norvaline dihydrochloride.

$^1$H-NMR(D$_2$O); δ: 0.33–0.36(2H,m), 0.64–0.66(2H,m), 1.09–1.14(2H,m), 1.76–2.07(4H,m), 3.10(2H,d,J=7.3 Hz), 3.42–3.47(2H,m), 4.09–4.13(1H,m); FAB-MS(m/z)246 (M$^+$+1)

Example 19

Synthesis of α-N-t-butoxycarbonyl-2-(2-S-methylisothioureidoethyl)qlycine-t-butyl ester hydroiodide Using α-N-t-butoxycarbonyl-2-(2-thioureidoethyl) glycine-t-butyl ester as a starting material and methyl iodide as a reagent, the same reaction as Example 1 was performed to yield 0.32 g of α-N-t-butoxycarbonyl-2-(2-S-methylisothioureidoethyl)glycine-t-butyl ester hydroiodide.

$^1$H-NMR(CDCl$_3$); δ: 1.45(9H,s), 1.49(9H,s), 1.77–2.06 (1H,m) 2.21–2.38(1H,m), 2.79(3H,s), 3.38–3.56(2H,m), 4.06–4.20(1H,m), 5.30–5.67(1H,m); FAB-MS(m/z)348 (M$^+$+1)

Example 20

Synthesis of 2-(2-S-methylisothioureidoethyl) qlycine dihydrochloride

Using as a starting material the compound obtained in Example 19, a deprotection was performed as in Example 4 to yield 0.18 g of 2-(2-S-methylisothioureidoethyl)glycine dihydrochloride.

$^1$H-NMR(D$_2$O); δ: 2.23–2.35(2H,m), 2.60(3H,s), 3.60–3.65(2H,m), 4.04–4.09(1H,m); FAB-MS(m/z)192 (M$^+$+1)

Example 21

Synthesis of α-N-t-butoxycarbonyl)-δ-(S-(3-chloroproyl) isothioureido)-L-norvaline-t-butyl ester hydroiodide Using 1-chloro-3-iodopropyl as a reagent, the same reaction as Example 1 was performed to yield 0.475 g of α-N-t-butoxycarbonyl-δ-(S-(3-chloropropyl)isothioureido )-L-norvaline-t-butyl ester hydroiodide.

$^1$H-NMR(CDCl$_3$); δ: 1.45(9H,S), 1.49(9H,s), 1.60–2.03 (4H,m), 2.18–2.32(2H,m), 3.35(2H,t,J=6.6 Hz), 3.46–3.65 (2H,m), 3.71–3.76(2H,m), 3.99–4.22(2H,m), 5.16(1H,m)

Example 22

Synthesis of δ-(S-(3-chloropropyl)isothioureido )-L-norvaline dihydrochloride

Using as a starting material the compound obtained in Example 21, a deprotection was performed as in Example 4 to yield δ-(S-(3-chloropropyl )isothioureido)-L-norvaline dihydrochloride.

$^1$H-NMR(DMSO-d$_6$); δ: 1.54–1.95(4H,m), 1.98–2.13 (2H,m), 3.22–3.65(4H,m), 3.69–3.78(2H,m), 3.85–3.98(1H, m)

The chemical structural formulae of the compounds of the Examples are shown in Table 1 to Table 3 below.

TABLE 1

| Example compound | Chemical structural formula |
|---|---|
| 1 | C$_2$H$_5$S-C(=NH)-NH-(CH$_2$)$_3$-CH(NHCOOt-Bu)-COOt-Bu · HI |
| 2 | C$_2$H$_5$S-C(=NH)-NH-(CH$_2$)$_3$-CH(NH$_2$)-COOH |
| 3 | FH$_2$CH$_2$CS-C(=NH)-NH-(CH$_2$)$_3$-CH(NHCOOt-Bu)-COOt-Bu · HBr |
| 4 | FH$_2$CH$_2$CS-C(=NH)-NH-(CH$_2$)$_3$-CH(NH$_2$)-COOH · 2HCl |
| 5 | CH$_2$=CHCH$_2$-S-C(=NH)-NH-(CH$_2$)$_3$-CH(NHCOOt-Bu)-COOt-Bu · HBr |
| 6 | CH$_2$=CHCH$_2$-S-C(=NH)-NH-(CH$_2$)$_3$-CH(NH$_2$)-COOH · 2HCl |

TABLE 2

| Example compound | Structural formula |
|---|---|
| 7 | 2-thiazolin-2-yl-NH-(CH$_2$)$_3$-CH(NHCOOt-Bu)-COOt-Bu · HBr |
| 8 | 2-thiazolin-2-yl-NH-(CH$_2$)$_3$-CH(NH$_2$)-COOH · 2HCl |

TABLE 2-continued

| Example compound | Structural formula |
|---|---|
| 9 | H3CS-C(=NH)-NH-(CH2)3-CH(NHCOOt-Bu)-COOt-Bu · HI |
| 10 | H3CS-C(=NH)-NH-(CH2)3-CH(NH2)-COOH · 2HCl |
| 11 | n-C3H7S-C(=NH)-NH-(CH2)3-CH(NHCOOt-Bu)-COOt-Bu · HI |
| 12 | n-C3H7S-C(=NH)-NH-(CH2)3-CH(NH2)-COOH |
| 13 | (tetrahydro-1,3-thiazin-2-yl)-NH-(CH2)3-CH(NHCOOt-Bu)-COOt-Bu · HBr |
| 14 | (tetrahydro-1,3-thiazin-2-yl)-NH-(CH2)3-CH(NH2)-COOH |
| 15 | (4-oxo-thiazolin-2-yl)-NH-(CH2)3-CH(NHCOOt-Bu)-COOt-Bu |

TABLE 3

| Example compound | Structural formula |
|---|---|
| 16 | (4-oxo-thiazolin-2-yl)-NH-(CH2)3-CH(NH2)-COOH |
| 17 | cyclopropyl-CH2-S-C(=NH)-NH-(CH2)3-CH(NHCOOt-Bu)-COOt-Bu · HBr |
| 18 | cyclopropyl-CH2-S-C(=NH)-NH-(CH2)3-CH(NH2)-COOH · 2HCl |
| 19 | H3CS-C(=NH)-NH-(CH2)2-CH(NHCOOt-Bu)-COOt-Bu · HI |
| 20 | H3CS-C(=NH)-NH-(CH2)2-CH(NH2)-COOH · 2HCl |
| 21 | ClH2CH2CH2CS-C(=NH)-NH-(CH2)3-CH(NHCOOt-Bu)-COOt-Bu · HI |
| 22 | ClH2CH2CH2CS-C(=NH)-NH-(CH2)3-CH(NH2)-COOH · 2HCl |

[Test Cases]

Compounds of the invention were evaluated for their inhibitory effect against NOS isoforms in comparison with the well known NOS inhibitors. The following were used as crude enzyme fractions of the respective NOS isoforms: a soluble fraction of the rat cerebral cortex for N-cNOS and a homogenate of cow pulmonary arterial endothelium cell (CPAE) for E-cNOS, whereas for iNOS, rats were administered lipopolysaccharide (LPS, 10 mg/kg, i.p.) and lungs were removed 6 h later to prepare soluble fractions.

The following NOS inhibitors were used as control compounds.

$N^G$-nitro-L-arginine (L-NNA), $N^G$-cyclopropyl-L-arginine (L-CPA), $N^G$-nitro-L-arginine methyl ester (L-NAME), $N^G$-amino-L-arginine (L-AA), $N^G$-iminoethyl-ornithine (L-NIO), $N^G$-monomethyl-L-arginine (L-NMMA), $N^G$-allyl-L-arginine (L-ALA), 7-nitroindazole (7-NI), and aminoguanidine (AG).

The crude enzyme sample of N-cNOS was prepared by the following procedure. Normal untreated male SD rats (body weight, 300–400 g) were decapitated; the whole brain was immediately removed from each animal and the cerebral cortex was separated on ice. Then, 5 volumes of 50 mM Tris-HCl containing 1 mM DTT (pH 7.4) was added and the mixture was homogenized for 3 min, followed by centrifugation at 1,000×g for 10 min. The resulting supernate was further centrifuged at 100,000×g for 60 min and a soluble cytosolic fraction of the finally obtained supernate was used as the crude enzyme sample of N-cNOS.

The crude enzyme sample of E-cNOS was prepared by the following procedure. A cow pulmonary arterial endothelium cell (CPAE) was cultured in a MEM medium containing 20% of FBS. Several days later, the cells were detached from the flask using a solution of 0.25% trypsin containing 1 mM EDTA and after addition of 0.1 M phosphate-buffered saline (PBS; pH 7.4) diluted with physiological saline, centrifugation was conducted at 1,000 rpm for 5 min. The supernate was then discarded and upon addition of a suitable amount of PBS, centrifugation was performed at 1,000 rpm for 5 min to wash the cells. The same procedure was repeated using 50 mM Tris-HCl containing 1 mM DTT (pH 7.4) to wash the cells. The precipitating cells were added an adequate amount of 50 mM Tris-HCl containing 1 mM DTT (pH 7.4) and the mixture was homogenized for 3 min to yield the crude enzyme sample of E-cNOS.

The crude enzyme sample of iNOS was prepared by the following procedure. Rats were administered intraperitoneally with LPS (10 mg/kg) and, 6 h later, perfused in a transcardiac manner with physiological saline containing 10 U/ml of heparin; thereafter, lungs were removed. Subsequently, 5 volumes of 50 mM Tris-HCl containing 1 mM DTT (pH 7.4) was added and the mixture was homogenized for 3 min, followed by centrifugation of the homogenate at 1,000×g for 10 min. The resulting supernate was centrifuged at 100,000×g for 60 min and a soluble cytosolic fraction of the finally obtained supernate was used as the crude enzyme sample of iNOS.

The method of measuring NOS activity was basically the same as already reported by the present inventors and consisted of determining quantitatively the conversion of a substrate L-[$^3$H] arginine to a reaction product L-[$^3$H] citrulline [Nagafuji et al., in Brain Edema IX (Ito et al. eds.) 60, pp. 285–288, 1994, Acta Neurochir., Springer-Verlag].

The reaction solution consisted of 100 μM L-[$^3$H] arginine, a prepared NOS enzyme (6–20 μg/ml protein), 1.25 mM CaCl$_2$, 1 mM EDTA, 10 μg/ml calmodulin, 1 mM NADPH, 100 μM tetrahydrobiopterine, 10 μM FAD, 10 μM FMN and 50 mM Tris-HCl (pH 7.4), to which one of the compounds of the invention or one of the control compounds was added.

The reaction was started by addition of L-[$^3$H] arginine and following incubation at 37° C. for 10 min, the reaction was terminated by addition of 2 ml of 50 mM Tris-HCl (pH 5.5) containing 1 mM EDTA and placing the mixture on ice. The reaction solution was passed through a cation-exchange resin column (Dowex AG50WX-8, Na$^+$ form, 3.2 ml) to separate the reaction product L-[$^3$H] citrulline from the unreacted residual substrate L-[$^3$H] arginine. The elute was combined with another elute resulting from the passage of distilled water (3 ml) through the column and put into a mini vial for recovery of L-[$^3$H] citrulline. Thereafter, 5 ml of a scintillation fluid was added and the contained radioactivity was measured with a liquid scintillation counter to determine the amount of L-[$^3$H] citrulline. The protein concentration of each crude enzyme sample was determined with a micro-assay kit of Biorad Co.

Table 4 lists the values of IC$_{50}$ (the concentration necessary to inhibit 50% activity), of all test compounds against each NOS isoform, as well as their respective ratios to each other; N-cNOS vs E-cNOS and N-cNOS vs iNOS as an index of selectivity. All data in Table 4 are expressed by mean ± standard error, with the number of cases indicated within parentheses.

TABLE 4

IC$_{50}$ Values of Test Compounds Against Three NOS Isoforms

| | IC$_{50}$ value (nM) | | | Ratio of I$_{50}$ values | |
| --- | --- | --- | --- | --- | --- |
| Test Compound | N-cNOS | E-cNOS | iNOS | E-cNOS/ N-cNOS | iNOS/ N-cNOS |
| Example 2 | 8.4 ± 0.7(3) | 492.1 ± 315.0(2) | 6,760.8(1) | 58.6 | 804.9 |
| Example 4 | 10.5 ± 0.8(3) | 1,311.9 ± 161.9(2) | 500.7(1) | 124.9 | 47.7 |
| L-NNA | 16.9 ± 3.6(4) | 89.8 ± 28.7(3) | 3,464.3 ± 198.5(3) | 5.3 | 205.0 |
| L-CPA | 27.3 ± 6.6(3) | 1,477.9 ± 580.0(3) | 7,153.9 ± 2,735.7(3) | 54.1 | 262.0 |
| L-NAME | 79.4 ± 11.6(3) | 985.4 ± 389.8(3) | 13,533.1 ± 9,751.3(4) | 12.4 | 170.4 |
| Example 6 | 112.8 ± 6.0(3) | 1,177.5 ± 51.6(2) | 298.2(1) | 10.4 | 2.6 |
| L-AA | 152.5 ± 55.7(3) | 523.5 ± 61.4(3) | 1,281.0 ± 440.9(3) | 3.4 | 8.4 |
| L-NIO | 277.0 ± 58.7(3) | 2,225.5 ± 112.6(3) | 457.8 ± 85.8(3) | 8.0 | 1.7 |
| L-NMMA | 337.8 ± 24.7(3) | 950.7 ± 232.1(3) | 3,480.9 ± 1,002.2(3) | 2.8 | 10.3 |
| Example 8 | 563.6 ± 283.8(2) | 3,316.3 ± 1,223.1(2) | 5,411.3(1) | 5.9 | 9.6 |
| L-ALA | 992.0 ± 162.4(3) | 15,053.4 ± 8,529.6(3) | 12,001.0 ± 2,632.4(3) | 15.2 | 12.1 |
| Example 10 | 1,255.3 ± 926.9(2) | 6,410.4 ± 1,247.3(2) | 10,449.6(1) | 5.1 | 8.3 |
| Example 12 | 1,339.9 ± 630.8(2) | 12,456.6(1) | 4,504.0(1) | 9.3 | 3.4 |
| 7-NI | 4,823.6 ± 985.2(3) | 2,132.7 ± 793.8(3) | 6,926.0 ± 1,405.1(2) | 0.4 | 1.4 |
| AG | 20,262.9 ± 4,172.6(3) | >100,000(3) | 27,207.8 ± 4,914.1(3) | >4.9 | 1.3 |

From Table 4, the following are clear:
1. The compounds of Examples 2 and 4 have a stronger N-cNOS inhibitory effect than the existing NOS inhibitors;
2. From a viewpoint of the selectivity for N-cNOS or E-cNOS, the compounds of Examples 2 and 4 show more selective inhibitory effect on N-cNOS compared with the existing NOS inhibitors.
3. From a viewpoint of the selectivity for N-cNOS or iNOS, the compound of Example 2 shows outstandingly more selective inhibitory effect on N-cNOS compared with the existing NOS inhibitors.
4. The compound of Example 6 has a by far stronger iNOS inhibitory effect than the existing NOS inhibitors.
5. From a viewpoint of the selectivity for N-cNOS or iNOS, the compound of Example 6 shows an extremely high selective inhibitory effect on iNOS.

Industrial Applicability

The compounds of the invention have a by far superior action in the selective inhibition of brain N-cNOS compared with the existing NOS inhibitors and, hence, are useful as therapeutics for treating cerebrovascular disorders (particularly as therapeutics for use in an acute phase of occlusive cerebrovascular disorders). In particular, the compounds of Examples 2 and 4 not only have a strong brain N-cNOS inhibitory effect but in terms of the selectivity for N-cNOS or E-cNOS, they also have outstandingly high selective inhibitory effect on brain N-cNOS and, hence, are useful as therapeutics of cerebrovascular disorders (particularly for use as therapeutics in an acute phase of occlusive cerebrovascular disorders).

In addition, the compounds of the invention have a by far superior action in the selective inhibition of iNOS compared with the existing NOS inhibitors and, hence, are useful as therapeutics of hypotension in sepsis. In particular, the compound for treating Example 6 not only has a strong iNOS inhibitory effect but in terms of the selectivity for N-cNOS or iNOS, it also has high selective inhibitory effect on iNOS and, hence, is useful as a therapeutic of hypotension in sepsis.

We claim:

1. A compound represented by the general formula (I):

$$R_4-N=C(SR_3)-NH-(CH_2)_n-CH(NHR_1)(COOR_2) \quad (I)$$

(where

R$_1$, denotes a hydrogen atom, a straight-chained or branched alkoxycarbonyl group having 1–6 carbon atoms in which the alkyl portion may optionally have a substituent, or an optionally substituted straight-chained or branched acyl group having 1–9 carbon atoms;

R$_2$ denotes a hydrogen atom or an optionally substituted straight-chained or branched alkyl group having 1–6 carbon atoms;

R$_3$ denotes an optionally substituted straight-chained or branched alkyl group having 1–6 carbon atoms or an optionally substituted straight-chained or branched alkenyl group having 2–6 carbon atoms;

R$_4$ denotes a hydrogen atom;

or alternatively R$_3$ and R4 may combine together to form an optionally substituted 5- to 7-membered ring; and n denotes an integer of 2–4, provided that when R$_3$ is a methyl group, n is not 3 at the same time) or a pharmaceutically acceptable salt thereof with the proviso that compounds having the formula (I) where R$_1$ and R$_2$ are each a hydrogen atom, R$_3$ is a straight-chained or branched alkyl group having 1–5 carbon atoms, R$_4$ is a hydrogen atom and n is an integer of 3 or 4 are excluded.

2. A compound as set forth in claim 1 which is represented by the general formula (I):

$$R_4-N=C(SR_3)-NH-(CH_2)_n-CH(NHR_1)(COOR_2) \quad (I)$$

(where

R$_1$ denotes a hydrogen atom, a straight-chained or branched alkoxycarbonyl group having 1–6 carbon atoms in which the alkyl portion may optionally have a substituent, or an optionally substituted straight-chained or branched acyl group having 1–9 carbon atoms;

R$_2$ denotes a hydrogen atom or an optionally substituted straight-chained or branched alkyl group having 1–6 carbon atoms;

R$_3$ denotes a halogen-atom substituted straight-chained or branched alkyl group having 1–6 carbon atoms;

R$_4$ denotes a hydrogen atom; and n denotes an integer of 2–4) or a pharmaceutically acceptable salt thereof.

3. A compound which is represented by the formula (I):

$$R_4-N=C(SR_3)-NH-(CH_2)_n-CH(NHR_1)(COOR_2) \quad (I)$$

(where

R$_1$ denotes a hydrogen atom, a straight-chained or branched alkoxycarbonyl group having 1–6 carbon atoms in which the alkyl portion may optionally have a substituent, or an optionally substituted straight-chained or branched acyl group having 1–9 carbon atoms;

R$_2$ denotes a hydrogen atom or an optionally substituted straight-chained or branched alkyl group having 1–6 carbon atoms;

R$_3$ denotes a 2-fluoroethyl group;

R$_4$ denotes a hydrogen atom; and n denotes an integer of 2–4) or a pharmaceutically acceptable salt thereof.

4. A compound as set forth in claim 1 which is represented by the general formula (I):

$$R_4-N=C(SR_3)-NH-(CH_2)_n-CH(NHR_1)(COOR_2) \quad (I)$$

(where

R$_1$ and R$_2$ each independently denote a hydrogen atom;

R$_3$ denotes an optionally substituted straight-chained or branched alkyl group having 1–6 carbon atoms or an optionally substituted straight-chained or branched alkenyl group having 2–6 carbon atoms;

$R_4$ denotes a hydrogen atom;

or alternatively $R_3$ and $R_4$ may combine together to form an optionally substituted 5- to 7-membered ring; and n denotes an integer of 2–4, provided that when $R_3$ is a methyl group, n is not 3 at the same time) or a pharmaceutically acceptable salt thereof with the proviso that compounds having the formula (I) where $R_1$ and $R_2$ are each a hydrogen atom, $R_3$ is a straight-chained or branched alkyl group having 1–5 carbon atoms, $R_4$ is a hydrogen atom and n is an integer of 3 or 4 are excluded.

5. A compound which is selected from the group of compounds consisting of δ-(S-(2-fluoroethyl) isothioureido)-L-norvaline, δ-(S-ethylisothioureido)-L-norvaline and δ-(S-(3-chloropropyl)isothioureido)-L-norvaline, and a pharmaceutically acceptable salts thereof.

6. A method for treating cerebrovascular disorders comprising inhibiting brain N-cNOS comprising administering to a patient in need thereof an effective amount of δ-[S-(2-fluoroethyl)-isothioureido)-L-norvaline dihydrochloride.

7. A method for treating hypotension in sepsis comprising inhibiting i-NOS comprising administering to a patient in need thereof an effective amount of δ-[S-(2-propenyl) isothioureido)-L-norvaline dihydrochloride.

8. A compound selected from the group consisting of the compound of formula (I)

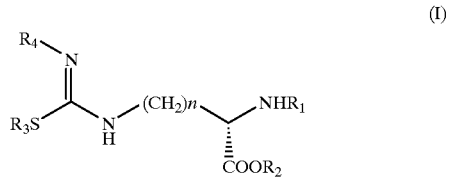

(I)

wherein $R_1$, $R_2$, and $R_4$ are hydrogen, $R_3$ is 2-propenyl and n is 3, and pharmaceutically acceptable salts thereof.

* * * * *